US008372176B2

(12) United States Patent
Schouteeten et al.

(10) Patent No.: US 8,372,176 B2
(45) Date of Patent: Feb. 12, 2013

(54) METAL COMPLEXES COMPRISING A LIGAND DERIVED FROM 2-ARYL-2-HYDROXYACETIC ACID AND A DIVALENT OR TRIVALENT METAL CATION, AND THEIR USE

(75) Inventors: Alain Schouteeten, Ezanville (FR); Sébastien Jus, Paris (FR); Claude Cathelineau, Vaujours (FR)

(73) Assignee: Clariant Specialty Fine Chemicals (France), Puteaux (FR)

( * ) Notice: Subject to any disclaimer, the term of this patent is extended or adjusted under 35 U.S.C. 154(b) by 835 days.

(21) Appl. No.: 12/301,806

(22) PCT Filed: May 21, 2007

(86) PCT No.: PCT/EP2007/054847
§ 371 (c)(1),
(2), (4) Date: Nov. 21, 2008

(87) PCT Pub. No.: WO2007/135109
PCT Pub. Date: Nov. 29, 2007

(65) Prior Publication Data
US 2010/0288004 A1 Nov. 18, 2010

(30) Foreign Application Priority Data

May 24, 2006 (FR) ..................... 06 04679

(51) Int. Cl.
*C05D 9/02* (2006.01)
(52) U.S. Cl. ............................. 71/27; 71/64.1
(58) Field of Classification Search ............ 71/27, 64.1
See application file for complete search history.

(56) References Cited

U.S. PATENT DOCUMENTS

| 3,960,536 A | 6/1976 | Dumont et al. |
| 4,978,784 A | 12/1990 | Christidis |
| 5,750,775 A | 5/1998 | Sidot et al. |

FOREIGN PATENT DOCUMENTS

| EP | 0987245 | 3/2000 |
| FR | 2244402 | 4/1975 |
| FR | 2638740 | 5/1990 |
| FR | 2759618 | 4/1997 |
| JP | 57-45134 | * 3/1982 |
| JP | 57045134 | 3/1982 |

OTHER PUBLICATIONS

English Translation of JP-57-45134, inventor Nishizawa Rinzo, published Mar. 13, 1982.
PTC International Search Report for PCT/EP2007/054847 mailed Jul. 30, 2007.
Database Beilstein, "Beilstein Institute for Organic Chemistry" Frankfurt-main, XP 002423372 Abstract & Gilliand et al. PR Oklahoma Acad, No. 21, p. 119; 1941.
Hoefnagel et al. "Metal Ion Catalysis in the Hydroxyalkylation of Phenol with Glyoxylic Acid," Recueil Des Travaux Chimiques Des Pays-Bas, Elsevier Science Publishers Amsterdam, NL vol. 7, No. 3; XP 000561981; pp. 242-247, Mar. 1, 1998.
English abstract of JP 57065134, Mar. 13, 1982.
PCT Written Opinion of the International Searching Authority for PCT/EP2007/054847, Jun. 23, 2008.
PCT International Preliminary Report on Patentability for PCT/EP2007/054847, Jun. 23, 2008.
Howard et al. "Chelating Agents" Kirk-Othmer Encyclopedia of Chemical Technology, vol. 5, pp. 708-739, 2004.

* cited by examiner

*Primary Examiner* — Wayne Langel
(74) *Attorney, Agent, or Firm* — Anthony A. Bisulca

(57) ABSTRACT

The invention relates to the use of metal complexes comprising a ligand derived from 2-aryl-2-hydroxyacetic acid and a divalent or trivalent metal cation and to the use of the said ligands in dissolving divalent or trivalent metal cations in aqueous phase.
The said complexes can be used to treat metal deficiencies in plants.

16 Claims, No Drawings

METAL COMPLEXES COMPRISING A LIGAND DERIVED FROM 2-ARYL-2-HYDROXYACETIC ACID AND A DIVALENT OR TRIVALENT METAL CATION, AND THEIR USE

The present invention relates to the use of ligands derived from 2-aryl-2-hydroxyacetic acid for solubilize divalent or trivalent metal cations, in aqueous phase, in a pH zone in which they are insoluble in a not complexed form.

The field of application of the present invention relates to the dissolution of metal entities. The majority of metal salts, such as $FeCl_3$ or $AlCl_3$, are solids which easily dissolve in water. However, the aqueous solutions obtained have an acidic pH due to the release of acid (HCl). For some applications, it is advantageous to simultaneously have metal entities in aqueous solution and a neutral or basic pH. In point of fact, it is known that some divalent or trivalent metal entities, such as Fe(III), Al(III), Cr(III) or Cu(II), do not exist in solution at neutral or basic pH values. Reference may be made to the Pourbaix diagrams (potential/pH diagrams), for example described in the book "Atlas d'équilibres électrochimiques [Atlas of Electrochemical Equilibria], Gauthier-Villars, Paris, 1963". For example, Fe(III) does not exist in solution for pH values of greater than 2 as, under these conditions, it exists predominantly in the $Fe(OH)_3$ form insoluble in the aqueous phase. For Al(III), the form $Al(OH)_3$ insoluble in the aqueous phase predominates for pH values of between 3 and 12 while, for Cu(II), the form $Cu(OH)_2$ insoluble in the aqueous phase predominates for pH values of greater than 6.

A specific application where it is advantageous to have metal entities in aqueous solution at a neutral or basic pH relates to the field of fertilizers used in agriculture. For example, iron deficiency (or iron chlorosis), which can result in a fall in yield for a wide range of agricultural crops, occurs particularly on alkaline soils, such as calcareous soils.

The use is known, in combating this problem, of chelates, for example described in the encyclopaedia "Kirk-Othmer, Encyclopedia of Chemical Technology, 5th edition, Vol. 5, pp. 708-739, 2004, Wiley".

The chelate [Fe(o,o-EDDHA)Na] is a product of choice in the prevention and treatment of iron chlorosis. The complexing of Fe(III) by the EDDHA (1,2-ethylenediamine-N,N'-bis (orthohydroxyphenylacetic) acid) makes it possible to obtain stable aqueous solutions at pH values of greater than or equal to 7. However, commercial chelates [Fe(o,o-EDDHA)Na] comprise a low level of iron, on average of the order of 6% by weight. Furthermore, for them to be applied to the plant (at the root or leaf), they can be dissolved in water. In point of fact, these commercial chelates are relatively insoluble, of the order of 150-300 g/l of water. Thus, the solutions prepared are very dilute and comprise a low level of iron (approximately from 9 to 18 g of iron per liter).

A search is thus still underway for methods which make it possible to obtain solutions having a higher content of metal salt, metal complexes or chelates having good solubility in water, and ligands exhibiting acceptable biodegradability.

In addition, the zone of pH in which the divalent or trivalent metal cation is insoluble in the free state, in a pH range which can go from the neutral pH to the basic pH, can differ according to the considered metal cation (see Pourbaix diagrams).

The technical problem to solve is thus to furnish ligands able to solubilize, in aqueous phase, divalent or trivalent metal cation at a pH, that is neutral or basic, and for which said cation is insoluble in its uncomplexed state.

In point of fact, the Applicant has discovered that the use of ligands derived from 2-aryl-2-hydroxyacetic acids makes it possible to solve the problems described above.

According to a first aspect, a subject-matter of the invention is thus the use of at least one compound of formula (I)

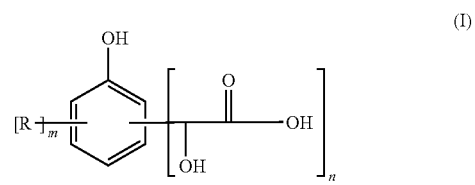

in which
R represents a halogen, an OH group, a COOH group, an $SO_3H$ group, a $PO_3H_2$ group, a CN group, an $NO_2$ group, a linear or branched $C_1$-$C_4$ alkyl group or a $C_1$-$C_4$ alkoxy group,
n has the value 1, 2 or 3,
m has a value from 0 to 5-n,
the group(s)

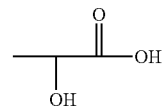

is (are) found in the ortho and/or para position with respect to the OH group of the phenyl ring,
and/or one of its salts,
in dissolving at least one divalent or trivalent metal cation in the aqueous phase at neutral or basic pH, in a pH zone in which said cation is insoluble in the uncomplexed state.

The term "dissolving at least one divalent or trivalent metal cation in the aqueous phase at neutral or basic pH" is understood to mean that the solubility of the considered metal cation, at the considered pH, when it is in the state of complex with a ligand made of a compound of formula (I), is increased compared to the value of solubility of the metal cation in a not complexed state, to be greater than 0.1% approximately, in particular greater than 1% approximately.

The term "salts of the compounds of formula (I)" is understood to mean that one or more of the salifiable functional groups, such as the carboxylic acid, phenol, $SO_3H$ or $PO_3H_2$ functional groups, is (are) salified.

Such salts are, for example, chosen from alkali metal salts, for example sodium or potassium, or ammonium salts.

The compounds of formula (I) can be salified according to techniques well known to a person skilled in the art, for example using inorganic bases (such as alkali metal or alkaline earth metal hydroxides), amines, ammonia or salts/acids, such as, for example, alkali metal or alkaline earth metal or ammonium carbonates, alkali metal or alkaline earth metal or ammonium hydrogencarbonates or alkali metal or alkaline earth metal or ammonium phenates.

In the present invention, the term "use of at least one compound of formula (I) and/or one of its salts" is understood to mean the fact that, when several compounds of formula (I) are used a mixture, they can, independently of one another, be salified or nonsalified.

In particular, a subject-matter of the present invention is a process for the dissolution of at least one divalent or trivalent metal cation in the aqueous phase at neutral or basic pH, in a pH zone in which said cation is insoluble in the uncomplexed state, characterized in that at least one compound of formula (I)

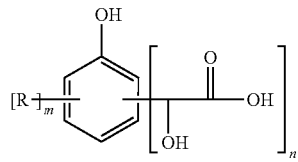

in which
R represents a halogen, an OH group, a COOH group, an $SO_3H$ group, a $PO_3H_2$ group, a CN group, an $NO_2$ group, a linear or branched $C_1$-$C_4$ alkyl group or a $C_1$-$C_4$ alkoxy group,
n has the value 1, 2 or 3,
m has a value from 0 to 5-n,
the group(s)

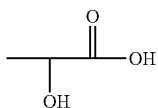

is (are) found in the ortho and/or para position with respect to the OH group of the phenyl ring,
and/or one of its salts,
is brought into contact, in the said aqueous phase, with at least one divalent or trivalent metal cation and, if necessary, the pH is adjusted to a neutral or basic pH value.

In particular, the said dissolution process comprises the stages consisting in:
preparing an aqueous solution of at least one compound of formula (I) as defined above and/or one of its salts,
adding, to the said solution, at least one divalent or trivalent metal cation, the order of the stages being unimportant, and
adjusting, if necessary, the pH to a neutral or basic pH value.

The molar ratio of the compound of formula (I) to the divalent or trivalent metal cation can, for example, be from 5/1 to 1/1, preferably from 2/1 to 1/1, in particular 1/1.

In the above formula (I), when R represents a halogen, it is, for example, a Cl, Br, F or I radical.

When R represents a linear or branched $C_1$-$C_4$ alkyl group, it denotes, for example, a methyl, ethyl, propyl, isopropyl, butyl, isobutyl, sec-butyl or tert-butyl radical.

When R represents a $C_1$-$C_4$ alkoxy group, it is, for example, a methoxy, ethoxy, propoxy or butoxy radical.

Suitable divalent metal cations comprise the Fe(II), Cu(II), Mg(II) and Cr(II) cations.

Suitable trivalent metal cations comprise the Fe(III), Cr(III) and Al(III) cations and very particularly the Fe(III) cation.

The said divalent or trivalent metal cations can, for example, be employed in the carbonate, chloride, bromide, iodide, sulphate, oxide, hydroxide, acetate or nitrate form, particularly in the chloride or sulphate form and more particularly in the sulphate form.

Under preferred conditions for implementation of the use or of the process which are described above, use is made of at least one compound of formula (I) in which m is equal to 0 and/or one of its salts.

Preferably, use is made of at least one compound of formula (I) in which
m is equal to 0,
n has the value 1 or 2,
the group(s)

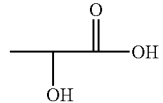

is (are) found in the ortho and/or para position with respect to the OH group of the phenyl ring,
and/or one of its salts.

In other preferred conditions for the implementation of the use or of the process which are described above, use is made of at least one compound of formula (I) in which:
m is equal to 0,
n has the value 1,
the group

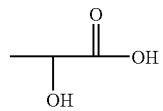

is found in the ortho or para position with respect to the OH group of the phenyl ring, and/or one of its salts.

Mention may be made, as examples of preferred compounds for the purposes of the invention, salified or nonsalified, of formula (I), of 2-(2-hydroxyphenyl)-2-hydroxyacetic acid (OHM), the sodium salt of 2-(2-hydroxyphenyl)-2-hydroxyacetic acid (OHMNa), the disodium salt of 2-(2-hydroxyphenyl)-2-hydroxyacetic acid (OHM.2Na), 2-(4-hydroxyphenyl)-2-hydroxyacetic acid (PHM), the sodium salt of 2-(4-hydroxyphenyl)-2-hydroxyacetic acid (PHMNa) or the disodium salt of 2-(4-hydroxyphenyl)-2-hydroxyacetic acid (PHM.2Na), in particular OHM and very particularly OHMNa and OHM.2Na or their mixtures.

The use and the dissolution process according to the invention are carried out under neutral or basic pH conditions under which the divalent or trivalent metal cations are particularly difficult to dissolve (see Pourbaix diagrams).

The term "neutral pH" is understood to mean a pH which is neutral (pH=7) or close to neutrality, for example within the range from 6 to 7.5.

In particular, the dissolution process according to the invention can comprise, after bringing into contact at least one compound of formula (I) and/or one of its salts and the divalent or trivalent metal cation, a stage of adjustment of the pH using a base. For this end, use may be made, for example, of a weak base, such as triethylamine, or a strong base, such as sodium or potassium hydroxide, depending on the pH desired. Starting from his general knowledge, a person skilled in the art is in a position to determine the base suitable for the adjustment desired.

Preferably, the pH is adjusted within a range from approximately 6 to 12, in particular 7.

Preferably, a strong base, such as sodium hydroxide, is used.

The metal cation can, for example, be employed in the form of an aqueous solution.

The compounds of formula (I) are known and commercially available products or can be prepared by application or adaptation of the methods described in the literature, such as, for example, in A. J Hoefnagel et al., Rec. Tray. Chem., 107, 242-7, (1988), or in Application FR 2 739 618. Generally, the products of formula (I) are obtained by condensation of glyoxylic acid with optionally substituted phenol, as disclosed, for example, in Application FR 2 638 740.

Mention may also be made of the PHMNa sold by Clariant Specialty Fine Chemicals (France).

A metal complex comprising at least one ligand derived from 2-aryl-2-hydroxyacetic acid and a divalent or trivalent metal cation in which the ligand is a compound of formula (I) and/or one of its salts as defined above can be prepared by a process comprising the stages consisting in bringing at least one compound of formula (I) and/or one of its salts into contact in the aqueous phase with a divalent or trivalent metal cation and in adjusting the pH to a neutral or basic pH value. The said metal complex is thus obtained in the aqueous phase. Alternatively, the said metal complex can be obtained in the powder form from the said aqueous solution by removing the water by standard techniques, for example by evaporation, atomization, lyophilization, and the like.

The invention also relates to the use of a metal complex comprising at least one ligand derived from 2-aryl-2-hydroxyacetic acid and a divalent or trivalent metal cation in which the ligand is a compound of formula (I) and/or one of its salts as defined above or of a composition comprising the said complex in the prevention or treatment of metal deficiency in plants.

The invention also relates, for the preceding use, all preferred aspects of compounds of formula (I) and/or one of its salts as defined above for the use in dissolving at least one divalent or trivalent metal cation in the aqueous phase at neutral or basic pH.

Especially, the said metal deficiency can consist of a deficiency in Fe(II), Cu(II), Mg(II), Cr(II), Fe(III), Cr(III) or Al(III).

In particular, this deficiency is iron chlorosis, and the use according to the invention aims to compensate a deficiency in Fe(II) or Fe(III), and more particularly in Fe(III).

The said composition can be presented in the powder form or in the form of an aqueous solution.

The invention also relates to the use of a metal complex comprising at least one ligand derived from 2-aryl-2-hydroxyacetic acid and a divalent or trivalent metal cation in which the ligand is a compound of formula (I) and/or one of its salts as defined above or of a composition comprising the said complex as fertilizer for plants.

The invention also relates, for the preceding use, all preferred aspects of compounds of formula (I) and/or one of its salts as defined above for the use in dissolving at least one divalent or trivalent metal cation in the aqueous phase at neutral or basic pH.

The said composition can be presented in the powder form or in the form of an aqueous solution.

The invention also relates to the use of a metal complex comprising at least one ligand derived from 2-aryl-2-hydroxyacetic acid and a divalent or trivalent metal cation in which the ligand is a compound of formula (I) and/or one of its salts as defined above or of a composition comprising the said complex as component of a phytopharmaceutical product comprising at least one active substance for the prophylactic or curative treatment of plants and to a phytopharmaceutical product comprising the said metal complex or the said composition.

The invention also relates, for the preceding use, all preferred aspects of compounds of formula (I) and/or one of its salts as defined above for the use in dissolving at least one divalent or trivalent metal cation in the aqueous phase at neutral or basic pH.

The said composition can be presented in the powder form or in the form of an aqueous solution.

The invention is illustrated without implied limitation by the following examples, in which the amounts of metals in solution were measured by ICP-OES (Inductively Coupled Plasma-Optical Emission Spectroscopy).

In the examples which follow, the term "theoretical % by weight of metal in solution" is understood to mean the ratio, expressed as percentage, of the total weight of metal initially introduced into the reaction medium to the weight of the filtrate recovered and analysed.

EXAMPLE 1

Dissolution of $FeCl_3$ with a Sodium Salt of 2-(2-Hydroxyphenyl)-2-Hydroxyacetic Acid (OHMNa)

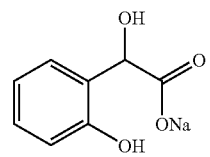

4.92 g (0.025 mol) of OHMNa are dissolved in 19.17 ml of water. 20.27 g of an aqueous solution comprising 6.76 g of $FeCl_3$ hexahydrate (0.025 mol) are added over 15 min while maintaining the temperature of the reaction medium at approximately 20° C. The pH of the solution is adjusted to 7 by addition of a 50% by weight aqueous sodium hydroxide solution (5.87 g). The mixture is subsequently stirred at ambient temperature for 24 h. After filtering and washing with water, 59.9 g of a solution with a dark brown-red colour are recovered.

2.3% by weight of Fe in solution are measured (theoretically 2.33% by weight).

This example shows that OHMNa makes it possible to obtain soluble Fe in the aqueous phase at pH 7.

COMPARATIVE EXAMPLE 1

8.11 g of $FeCl_3$ hexahydrate are dissolved in 12 ml of water. The pH is adjusted to 7 by addition of a 50% by weight aqueous sodium hydroxide solution. After filtering and washing with water, less than 10 ppm of Fe are measured in the filtrate.

EXAMPLE 2

Dissolution of $FeCl_3$ with 5-Chloro-2-Hydroxymandelic Acid

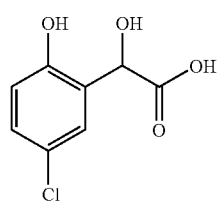 [SMILES: O=C(O)C(O)c1cc(Cl)ccc1O]

2.05 g (0.01 mol) of 5-chloro-2-hydroxymandelic acid are suspended in 15 ml of water. 0.8 g of 50% by weight sodium hydroxide solution (0.01 mol) is added in order to obtain a solution. 17.7 g of an aqueous solution comprising 2.7 g of $FeCl_3$ hexahydrate (0.01 mol) are added over 15 min while maintaining the temperature of the reaction medium at approximately 20° C. The pH of the solution is adjusted to 7 by addition of 2.4 g of a 50% by weight aqueous sodium hydroxide solution. The mixture is subsequently stirred at ambient temperature for 24 h. After filtering, 35.1 g of a solution with a dark brown-red colour are recovered.

1.3% by weight of Fe in solution are measured (theoretically 1.59% by weight).

This example shows that the ligand 5-chloro-2-hydroxymandelic acid makes it possible to obtain soluble Fe in aqueous phase at pH 7.

EXAMPLES 3 TO 6

The procedure of Example 1 or 2 is repeated but using, according to the invention, the ligands B, C, D and E of formula (I), the structures of which are described in Table 1 below, and varying the ligand/metal molar ratios, if appropriate.

TABLE 1

| Ligand | Structure |
|---|---|
| B | (4-hydroxyphenyl)(hydroxy)acetic acid sodium salt |
| C | 3-ethoxy-4-hydroxymandelic acid |
| D | 3,4-dihydroxymandelic acid |
| E | 2-hydroxy-5-fluoromandelic acid |

The results obtained are shown in Tables 2 and 3 below.

TABLE 2

| Example | Ligand | Amount of ligand (g) | Amount of $FeCl_3$ hexa-hydrate (g) | Weight of water (g) | Weight of NaOH added (g) | Weight of the filtrate (g) |
|---|---|---|---|---|---|---|
| 3 | B | 5.81 | 3.55 | 40 | 3.12 | 49.28 |
| 4 | C | 6.12 | 3.55 | 26 | 4.56 | 39.63 |
| 5 | D | 2.6 | 1.35 | 16 | 1.6 | 18.69 |
| 6 | E | 1.78 | 2.38 | 25.15 | 4 | 33.28 |

TABLE 3

| Example | Theoretical % by weight of Fe in solution | % by weight measured |
|---|---|---|
| 3 | 1.47 | 1.1 |
| 4 | 1.83 | 1.5 |
| 5 | 1.49 | 1.2 |
| 6 | 1.46 | 1.4 |

Examples 3 to 6 show that the use of the ligands B to E makes it possible to obtain a large amount of soluble Fe in the aqueous phase at pH 7.

COMPARATIVE EXAMPLES 2 TO 6

The procedure of Example 2 is repeated by using the compounds G, H, I and J as ligands, the structures of which are described in Table 4 below, and varying the ligand/metal molar ratios, if necessary.

TABLE 4

| Ligand | Structure |
|---|---|
| G | 2-hydroxyphenylacetic acid |
| H | 2-(2-hydroxyphenyl)-2-oxoacetic acid |
| I | mandelic acid |
| J | 2-chloromandelic acid |

The results obtained are shown in Tables 5 and 6 below.

TABLE 5

| Comparative Example | Ligand | Amount of ligand (g) | Amount of FeCl₃ hexa-hydrate (g) | Weight of water (g) | Weight of NaOH added (g) | Weight of the filtrate (g) |
|---|---|---|---|---|---|---|
| 2 | G | 1.24 | 2.16 | 18 | 2.34 | 15.51 |
| 3 | H | 2.99 | 3.28 | 15 | 3.26 | 16.39 |
| 4 | I | 1.54 | 2.7 | 20 | 3.2 | 23.42 |
| 5 | J | 2.47 | 3.55 | 15 | 5.4 | 15.36 |
| 6 | G | 1.98 | 1.72 | 21 | 2.86 | 20.08 |

TABLE 6

| Comparative Example | Theoretical % by weight of Fe in solution | % by weight measured |
|---|---|---|
| 2 | 2.88 | <0.0025 |
| 3 | 4.09 | 0.5 |
| 4 | 2.38 | 0.09 |
| 5 | 4.73 | 0.01 |
| 6 | 1.67 | 0.01 |

These comparative examples show that the compounds G, H, I and J do not make possible or make possible only to a very slight extent the dissolution of iron in aqueous solution at pH 7.

Comparative Example 6 shows a similar result even on using a ligand/iron molar ratio of 2/1.

EXAMPLES 7 TO 11

Dissolution of FeCl₃ with the Sodium Salt of 2-(2-Hydroxyphenyl)-2-Hydroxyacetic Acid (OHMNa) at Different pH Values The procedure described in Example 1 is repeated but adjusting the pH of the solution to 6, 7, 9, 10 and 12.

The results obtained are shown in Tables 7 and 8 below.

TABLE 7

| Example | Amount of ligand (g) | Amount of FeCl₃ hexahydrate (g) | Weight of water (g) | Weight of NaOH added (g) | pH | Weight of the filtrate (g) |
|---|---|---|---|---|---|---|
| 7 | 2.01 | 2.7 | 20 | 1.5 | 6 | 20.65 |
| 8 | 4.92 | 6.76 | 42.68 | 5.87 | 7 | 59.9 |
| 9 | 4.92 | 6.76 | 52.68 | 7.3 | 9 | 71.2 |
| 10 | 4.92 | 6.76 | 40 | 8 | 10 | 49.8 |
| 11 | 4.92 | 6.76 | 52.68 | 8 | 12 | 72.8 |

TABLE 8

| Example | Theoretical % by weight of Fe in solution | % by weight measured |
|---|---|---|
| 7 | 2.18 | 1.7 |
| 8 | 2.33 | 2.3 |
| 9 | 1.96 | 1.9 |
| 10 | 2.80 | 2.7 |
| 11 | 1.92 | 1.9 |

These examples show that the use of OHMNa makes it possible to obtain soluble Fe in the aqueous phase for pH values which are basic, neutral or close to neutrality.

EXAMPLE 12

Dissolution of FeCl₃ with the Disodium Salt of 2-(2-Hydroxyphenyl)-2-Hydroxyacetic Acid (OHM.2Na)

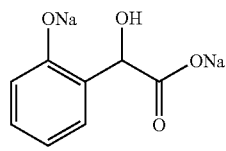

A solution composed of 40 g of water and of 12.97 g of FeCl₃ hexahydrate (0.048 mol) is added over 15 min to 43.5 g of an aqueous solution comprising 10.2 g of OHM.2Na (0.048 mol) while maintaining the temperature of the reaction medium at approximately 20° C. The pH of the solution is adjusted to 7 by addition of a 50% by weight aqueous sodium hydroxide solution (5.1 g). The mixture is subsequently stirred at ambient temperature for 5 weeks without specific protection with regard to light. After filtering, 80 g of a solution with a dark brown-red colour are recovered.

3.2% by weight of Fe in solution are measured (theoretically 3.35% by weight).

This example shows that OHM.2Na makes it possible to dissolve iron in aqueous solution at pH 7 and in a lasting manner.

EXAMPLE 13

Dissolution of FeCl₃ with OHMNa in the Presence of Calcium Carbonate CaCO₃

1.98 g (0.01 mol) of OHMNa are dissolved in 8 ml of water.
12.7 g of an aqueous solution comprising 2.7 g of FeCl₃ hexahydrate (0.01 mol) are added over 15 min while maintaining the temperature of the reaction medium at approximately 20° C. The pH of the solution is adjusted to 7 by addition of 2.3 g of a 50% by weight aqueous sodium hydroxide solution. A suspension of 1.0 g (0.01 mol) of CaCO₃ in 15 g of water is subsequently added. A few drops of 37% HCl are added to adjust the pH to 7. The mixture is subsequently stirred at ambient temperature for 24 hours. After filtering, 35.0 g of a solution with a dark brown-red colour are recovered.

1.4% by weight of Fe in solution are measured (theoretically 1.59% by weight).

This example shows that the ligand OHMNa makes it possible to obtain soluble Fe in the aqueous phase at pH 7 despite the presence of CaCO₃.

EXAMPLE 14

The dark brown-red solution obtained in Example 1 is concentrated by distillation of water. The residue is dried in an oven at 50° C. for 48 h. A red-brown powder is obtained which comprises 12% by weight of iron by ICP-OES measurement.

A measurement on a powder formed of [Fe(o,o-EDDHA)Na] chelate available commercially gives only 7.8% by weight of iron.

This example shows that the use of OHMNa makes it possible to very greatly increase the content of iron in comparison with the product available commercially.

EXAMPLE 15

Solubility Study on the OHMNa/Fe Complex 10 g of the powder obtained in Example 14 are dissolved in 19 ml of water. After filtering, a solution with a dark brown-red colour comprising 4.1% by weight of iron in solution is recovered.

By comparison, the use of a chelate available commercially [Fe(o,o-EDDHA)Na] makes it possible to prepare an aqueous solution comprising at best a level of iron of 9-18 µl, that is to say 0.9-1.8% by weight.

EXAMPLES 16 TO 18

Dissolution of Al(III), Cr(III) and Cu(II) Cations with OHMNa

The procedure of Example 1 is repeated but substituting $FeCl_3$ by $AlCl_3$, $CrCl_3.6H_2O$ and $Cu(OAc)_2.H_2O$ respectively.

The results obtained are given in Tables 9 and 10 below.

TABLE 9

| Example | Amount of ligand (g) | Metal | Amount of metal (g) | Weight of water (g) | Weight of NaOH added (g) | Weight of the filtrate (g) |
|---|---|---|---|---|---|---|
| 16 | 2.01 | $AlCl_3$ | 1.35 | 20 | 2.4 | 26.29 |
| 17 | 2.01 | $CrCl_3$ | 2.72 | 20 | 2.4 | 22.27 |
| 18 | 2.01 | $Cu(OAc)_2$ | 2.04 | 40 | 1.4 | 44.58 |

TABLE 10

| Example | Theoretical % by weight of metal in solution | % by weight measured |
|---|---|---|
| 16 | 1 | 1 |
| 17 | 1.83 | 1.40 |
| 18 | 1.43 | 1.40 |

Examples 16 to 18 show that OHMNa makes it possible to obtain soluble Al, soluble Cr and soluble Cu in the aqueous phase at pH 7 for at least 24 h.

EXAMPLE 19

Dissolution of Mg(II) Cations with OHM.2Na

To an aqueous solution (60 g) containing 0.05 mol of OHM.2Na, are added 9.9 g of an aqueous solution containing 0.025 mole of magnesium chloride ($MgCl_2$). The pH is set at 12 with 1 g of an aqueous solution of HCl 1N. After 24 hours under stirring, the solution is still homogeneous, without any solid. Without the OHM.2Na, the magnesium precipitate at pH 12 as a white solid ($Mg(OH)_2$).

EXAMPLE 20

Dissolution of Mg(II) Cations with OHM.2Na

To an aqueous solution (60 g) containing 0.05 mol of OHM.2Na, are added 19.8 g of an aqueous solution containing 0.05 mole of magnesium chloride ($MgCl_2$). The pH is set at 12 with 2.6 g of an aqueous solution of NaOH 30%. After 24 hours under stirring, the solution is still homogeneous, without any solid. Without the OHM.2Na, the magnesium precipitate at pH 12 as a white solid ($Mg(OH)_2$).

EXAMPLE 21

The effectiveness of the metal complexes of the present invention in treating metal chlorosis in plants is illustrated in the following comparative runs, performed in a greenhouse test, using calcareous Issirac soil. The Chlorotic Power Index of this soil is 1400. Eight germinated chlorotic Syrah vine grafts were planted in 1 Kg pots. Four plants were treated each with 10 mL of an aqueous solution prepared with the iron complex powder obtained according to example 14. In each 10 mL, the iron complex quantity was equivalent to 1 mg of pure iron. The other four plants did not receive any iron source and were used as control plants. Once a month, all the plants received nutrient solution containing 0% iron. When the plants started to grow, the chlorophyll fluorescence was measured on each plant. These measurements gave the evolution of the quantum yield of chlorophyll fluorescence that is shown in the following table 11. It can be considered as a parameter of plant vitality.

TABLE 11

| | Days | | | | | | | | | |
|---|---|---|---|---|---|---|---|---|---|---|
| | 0 | 2 | 7 | 15 | 22 | 29 | 34 | 42 | 51 | 57 |
| Control plants | 0.802 | 0.801 | 0.806 | 0.814 | 0.817 | 0.810 | 0.780 | 0.740 | 0.696 | 0.648 |
| Plants treated with iron complex | 0.812 | 0.814 | 0.808 | 0.803 | 0.804 | 0.806 | 0.800 | 0.782 | 0.763 | 0.757 |

It can be seen that the quantum yield can be preserved at a high value for the plants initially treated with iron complex prepared in example 14, while, for control plants, which have not received any iron treatment, the quantum yield of chlorophyll fluorescence is plummeting. The visual comparison is also striking: the un-treated plants had a very low development and showed a high chlorotic level, while the treated plants grew normally with a low chlorotic level.

These results demonstrate that the use of the iron complex prepared according to example 14 is an efficient treatment of iron chlorosis.

The invention claimed is:

1. A method for preventing or treating a metal deficiency in plants comprising the step of providing a plant with an effective amount of at least one metal complex comprising
   a) at least one ligand derived from 2-aryl-2-hydroxyacetic acid in which the ligand is a compound of formula (I)

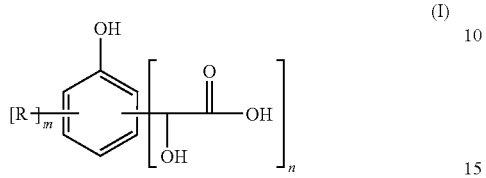

(I)

wherein
   R is a halogen, an OH group, a COOH group, an $SO_3H$ group, a $PO_3H_2$ group, a CN group, an $NO_2$ group, a linear or branched $C_1$-$C_4$ alkyl group or a $C_1$-$C_4$ alkoxy group,
   n has the value 1, 2 or 3,
   m has a value from 0 to 5-n,
   the group

is found in the ortho position, para position or both with respect to the OH group of the phenyl ring,
   one of its alkali metal salts or ammonium salts or a mixture thereof,
   and
   b) a divalent or trivalent metal cation.

2. The method according to claim 1, wherein m is equal to 0.

3. The method according to claim 1, wherein
   m is equal to 0, and
   n has the value 1 or 2.

4. The method according to claim 1, wherein
   m is equal to 0, and
   n has the value 1.

5. The method according to claim 1, wherein the compound of formula (I) or one of its salts is selected from the group consisting of 2-(2-hydroxyphenyl)-2-hydroxyacetic acid (OHM), the sodium salt of 2-(2-hydroxyphenyl)-2-hydroxyacetic acid (OHMNa), the disodium salt of 2-(2-hydroxyphenyl)-2-hydroxyacetic acid (OHM.2Na), 2-(4-hydroxyphenyl)-2-hydroxyacetic acid (PHM), the sodium salt of 2-(4-hydroxyphenyl)-2-hydroxyacetic acid (PHMNa), the disodium salt of 2-(4-hydroxyphenyl)-2-hydroxyacetic acid (PHM.2Na), and their mixtures.

6. The method according to claim 1, wherein the metal cation is selected from the group consisting of Fe(II), Cu(II), Mg(II), Cr(II), Fe(III), Cr(III) and Al(III).

7. The method according to claim 1, wherein the metal cation is Fe(III).

8. The method according to claim 1, wherein the at least one metal complex is either in the form of a powder, an aqueous solution or as a composition comprising the at least one metal complex in the form of a powder or aqueous solution.

9. A method for fertilizing a plant comprising the step of providing a plant with an effective amount of at least one metal complex comprising
   a) at least one ligand derived from 2-aryl-2-hydroxyacetic acid in which the ligand is a compound of formula (I)

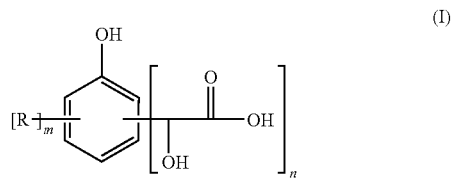

(I)

wherein
   R is a halogen, an OH group, a COOH group, an $SO_3H$ group, a $PO_3H_2$ group, a CN group, an $NO_2$ group, a linear or branched $C_1$-$C_4$ alkyl group or a $C_1$-$C_4$ alkoxy group,
   n has the value 1, 2 or 3,
   m has a value from 0 to 5-n,
   the group

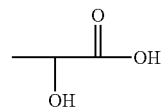

is found in the ortho position, para position or both with respect to the OH group of the phenyl ring,
   one of its alkali metal or ammonium salts or a mixture thereof,
   and
   b) a divalent or trivalent metal cation.

10. The method according to claim 9, wherein m is equal to 0.

11. The method according to claim 9, wherein
    m is equal to 0, and
    n has the value 1 or 2.

12. The method according to claim 9, wherein
    m is equal to 0, and
    n has the value 1.

13. The method according to claim 9, wherein the compound of formula (I) or one of its salts is selected from the group consisting of 2-(2-hydroxyphenyl)-2-hydroxyacetic acid (OHM), the sodium salt of 2-(2-hydroxyphenyl)-2-hydroxyacetic acid (OHMNa), the disodium salt of 2-(2-hydroxyphenyl)-2-hydroxyacetic acid (OHM.2Na), 2-(4-hydroxyphenyl)-2-hydroxyacetic acid (PHM), the sodium salt of 2-(4-hydroxyphenyl)-2-hydroxyacetic acid (PHMNa), the disodium salt of 2-(4-hydroxyphenyl)-2-hydroxyacetic acid (PHM.2Na), and their mixtures.

14. The method according to claim 9, wherein the metal cation is selected from the group consisting of Fe(II), Cu(II), Mg(II), Cr(II), Fe(III), Cr(III) and Al(III).

15. The method according to claim 9, wherein the metal cation is Fe(III).

16. The method according to claim 9, wherein the at least one metal complex is either in the form of a powder, an aqueous solution or as a composition comprising the at least one metal complex in the form of a powder or aqueous solution.

* * * * *